US005691377A

United States Patent [19]

Estienne et al.

[11] Patent Number: 5,691,377
[45] Date of Patent: Nov. 25, 1997

[54] USE OF N-METHYL-ASPARTIC ACID FOR ENHANCING GROWTH AND ALTERING BODY COMPOSITION

[75] Inventors: Mark Joseph Estienne; Jeannine Marie Harter-Dennis, both of Salisbury, Md.; Mark Newcombe, Ontario, Canada; Claude Richard Barb, Athens, Ga.; John Palmer McMurtry, Columbia; Thomas Gray Hartsock, Damascus, both of Md.

[73] Assignees: University of Maryland Eastern Shore and University of Maryland College Park, College Park, Md.; The United States of America as represented by the Secretary of Agriculture, Washington, D.C.; a part interest

[21] Appl. No.: 274,880

[22] Filed: Jul. 14, 1994

Related U.S. Application Data

[63] Continuation-in-part of Ser. No. 99,576, Jul. 30, 1993, abandoned.

[51] Int. Cl.$^6$ .................. A61K 31/195; A61K 31/74; A61K 38/102
[52] U.S. Cl. .................. 514/557; 426/656; 426/805; 426/807; 514/2; 514/12; 530/350
[58] Field of Search ................ 514/557; 426/656, 426/805–807

[56] References Cited

U.S. PATENT DOCUMENTS

| | | |
|---|---|---|
| 3,598,122 | 8/1971 | Zaffarone . |
| 3,598,123 | 8/1971 | Zaffarone . |
| 4,286,592 | 9/1981 | Chandrasekaran . |
| 4,314,557 | 2/1982 | Chandrasekaran . |
| 4,379,454 | 4/1983 | Campbell et al. . |
| 4,568,343 | 2/1986 | Leeper et al. . |
| 4,758,434 | 7/1988 | Kydonieus et al. . |
| 4,781,924 | 11/1988 | Lee et al. . |

OTHER PUBLICATIONS

Estienne et al., "N–Methyl–D, L–Aspartate Stimulates Growth Hormone by not Luteinizing Hormone Secretion in the Sheep", *Life Sciences* 44:1527–1533, 1989.
Estienne et al., "Growth Hormone Release After N–Methyl–D, L–Aspartate in Sheep: Dose Response and Effect of an Opioid Antagonist", *J. Anim. Sci.* 68:3198–3203.
Estienne et al., "Growth Hormone and Luteinizing Hormone Concentrations in Serum of Barrows Treated with N–Methyl-Aspartate", *J. Anim. Sci.* In Press.
Estienne et al., "Effect of N–Methyl–d, L–Aspartate on Luteinizing Hormone Secretion in Ovariectomized Ewes in the Absence and Presence of Estradiol", *Biology of Reproduction* 42:126–130.
Plant et al., "Puberty in Monkeys is Triggered by Chemical Stimulation of the Hypothalamus", *Proc. Natl. Acad. Sci. USA* 86:2506–2510, 1989.

Price et al., "Acute Elevations of Serum Luteinizing Hormone Induced by Kainic Acid, N–Methyl Aspartic Acid or Homocysteic Acid", *Neuroendocrinology*. 26:352–358, 1978.
Sesti et al., "Elicitation of Release of Luteinizing Hormone by N–Methyl–D, L–Aspartic Acid During Three Paradigms of Suppressed Secretion of Luteinizing Hormone in the Female Pig", *Domest. Anim. Endocrinol.* 9:105–114, 1992.
Wilson et al., "Acute Effects of N–methyl–D, L–Aspartate on the Release of Pituitary Gonadotropin and Prolactin in the Adult Female Rhesus Monkey", *Brain Res.* 248: 177–179, 1992.
Urbanski, "A Role for N–Methyl–d–Aspartate Receptors in the Control of Seasonal Breeding", *Endocrinology* 127:2223–2228, 1982.
Reyes et al., "Unexpected Inhibitory Action of N–Methyl–D, L–Aspartate on Luteinizing Hormone Release in Adult Ovariectomized Rhesus Monkeys: A Role of Hypothalamic–Adrenal Axis", *The Endocrine Society*, 0013–7227/90/1272–0724, 1990.
Price et al., "Reversible Action of N–methyl Aspartate on Gonadotrophin Neuroregulation", *Brain Research*, 176 165–168, 1979.
Gay et al., "Sustained Intermittent Release of Gonadotropin–Releasing Hormone in the Prepubertal Male Rhesus Monkey Induced by N–Methyl–D, L–Aspartic Acid", *Neuroendocrinology*. 48:147–152, 1988.
Gay et al., "N–Methyl–D, L–Aspartate Elicits Hypothalamic Gonadotropin–Releasing Hormone Release in Prepubertal Male Rhesus Monkeys (Macaca mulatta)", *Endocrinology*, 0013–7227/87/1206–2289, 1987.
Pohl et al., "Qualitative Changes in Luteinizing Hormone and Prolactin Responses to N–Methyl–Aspartic Acid During Lactatiion in the Rat", *Endocrinology*, 0013, 7227/89/ 1244–1905, 1989.
Urbanski et al., "Activation of Luteinizing Hormone–Releasing Hormone Release Advances the onset of Female Puberty", *Neuroendocrinology* 46:273–276, 1987.
Farah et al., "N–Methyl–D–Aspartate Treatment Increases Circulating Adrenocorticotropin and Luteinizing Hormone in the Rat", *Endocrinology*, 0013–7227/91/1284–1875, 1991.
Cicero et al., "Characterization and Possible Opioid Modulation of N–Methyl–D–Aspartic Acid Induced Increases in Serum Luteinizinng Hormone Levels in the Developing Male Rat", *Life Sciences*, vol. 42, pp. 1725–1732, 1988.

(List continued on next page.)

*Primary Examiner*—Shep K. Rose
*Attorney, Agent, or Firm*—Oblon, Spivak, McClelland, Maier & Neustadt, P.C.

[57] ABSTRACT

N-methyl-aspartic acid (NMA) is used to increase the growth rate, feed efficiency and/or decrease the amount of body fat of an animal, such as a chicken, pig, fish or human. Administration of NMA can be via injection or can be oral or transdermal administration or via subcutaneous implant.

13 Claims, No Drawings

OTHER PUBLICATIONS

Bourguignon et al., "Maturation of the Hypothalamic Control of Pulsatile Gonadotropin–Releasing Hormone Secretion at Onset of Puberty. I. Increased Activation of N–Methyl–d–Aspartate Receptors", *Endocrinology*, 0013–7227/90/1272–087, 1990.

Johnson et al., "The Effect of Human Growth Hormone–Releasing Factor or Porcine Somatotropin or Serum Hormones and Metabolites, Growth Performance and Carcass Traits in Swine". *J. Anim. Sci.* 68:3204–3211, 1990.

Etherton et al., "Stimulation of Pig Growth Performance by Porcine Growth Hormone and Growth Hormone–Releasing Factor" *J. Anim. Sci.* 63:1389–1399, 1986.

USE OF N-METHYL-ASPARTIC ACID FOR ENHANCING GROWTH AND ALTERING BODY COMPOSITION

CROSS REFERENCE TO RELATED APPLICATION

This application is a continuation-in-part of U.S. patent application Ser. No. 08/099,576, filed Jul. 30, 1993 now abandoned.

BACKGROUND OF THE INVENTION

The present invention relates generally to the use of hormone stimulating substances which affect body composition and/or, particularly in the case of animal husbandry, the production of meat products. Specifically, the invention relates to the use of N-methyl-aspartic acid (NMA) to stimulate the endogenous secretion of hormones, including growth hormone (GH), insulin-like growth factor (IGF-1) and triiodothyronine (T3) which are involved in the production of milk, eggs and meat in domesticated animals. In use in humans, in particular, NMA can affect growth, feed efficiency and body fat composition.

The art of animal husbandry has long sought various methods for increasing the amount and/or efficiency of production of meat and related animal products from domesticated animals. Such methods include selective breeding and feeding regimens, as well as the administration of various drugs and hormones. Growth hormone, for example, has been shown under certain conditions to increase the growth rate of some animals if administered over a period of time.

In particular, exogenous GH injection is known to improve the rate and efficiency of growth, and to decrease the amount of body fat in pigs. To provide this effect, however, GH must be administered by injection periodically into the animal. Other avenues of administration, such as oral ingestion, are not feasible due to the breakdown of GH in the stomach and intestine of the animal prior to its absorption into the blood stream. Repeated injections of growth hormone, however, is prohibitively expensive, both from the standpoint of cost and the labor involved in administration.

Publications disclosing the injection of GH include Johnson et al, "The Effect of Human Growth Hormone-Releasing Factor or Porcine Somatotropin on Serum Hormones and Metabolites, Growth Performance and Carcass Traits in Swine", *J. Anim. Sci.* 68:3204–3211, 1990, and Etherton et al, "Stimulation of Pig Growth Performance by Porcine Growth Hormone and Growth Hormone-Releasing Factor", *J. Anim. Sci.* 63:1389–1399, 1986.

It is also known that certain amino acids can affect hormone levels. For example, N-methyl-aspartic acid (NMA) can, via injection, be used to increase the secretion of certain hormones, including growth hormone. Publications disclosing the injection of NMA include the following:

Estienne et al, "N-Methyl-D,L-Aspartate Stimulates Growth Hormone but not Luteinizing Hormone Secretion in the Sheep", *Life Sciences* 44:1527–1533, 1989.

Estienne et al, "Growth Hormone Release After N-Methyl-D,L-Aspartate in Sheep: Dose Response and Effect of an Opioid Antagonist", *J. Anim. Sci.* 68:3198:3203, 1990.

Estienne et al, "Effect of N-Methyl-d,l-Aspartate on Luteinizing Hormone Secretion in Ovariectomized Ewes in the Absence and Presence of Estradiol", *Biology of Reproduction* 42:126–130, 1990.

Plant et al, "Puberty in monkeys is triggered by chemical stimulation of the hypothalamus", *Proc. Natl. Acad. Sci USA* 86:2506–2510, 1989.

Price et al, "Acute Elevations of Serum Luteinizing Hormone Induced by Kianic Acid, N-Methyl Aspartic Acid or Homocysteic Acid", *Neuroendocrinology* 26:352–358, 1978.

Sesti et al, "Elicitation of Release of Luteinizing Hormone by N-Methyl-D,L-Aspartic Acid During Three Paradigms of Suppressed Secretion of Luteinizing Hormone in the Female Pig", *Domest. Anim. Endocrinol.* 9:105–114, 1992.

Wilson et al, "Acute Effects of N-methyl-D,L-Aspartate on the Release of Pituitary Gonadotropin and Prolactin in the Adult Female Rhesus Monkey", *Brain Res.* 248:177–179, 1982.

Urbanksi, "A Role for N-Methyl-d-Aspartate Receptors in the Control of Seasonal Breeding", *Endocrinology* 127:2223–2228, 1990.

Reyes et al, "Unexpected Inhibitory Action of N-Methyl-D,L-Aspartate on Luteinizing Hormone Release in Adult Ovariectomized Rhesus Monkeys: A Role of the Hypothalamic-Andrenal Axis", *The Endocrine Society* 0013-7227/90/1272-0724, 1990.

Price et al, "Reversible action of N-methyl aspartate on gonadotrophin neuroregulation", *Brain Research* 176:165–168, 1979.

Gay et al, "Sustained Intermittent Release of Gonadotropin-Releasing Hormone in the Prepubertal Male Rhesus Monkey Induced by N-Methyl-D,L-Aspartic Acid", *Neuroendocrinology* 48: 147–152, 1988.

Gay et al, "N-Methyl-d,l-Aspartate Elicits Hypothalamic Gonadotropin-Releasing Hormone Release in Prepubertal Male Rhesus Monkeys (Macaca mulatta)", *Endocrinology* 0013-7227/87/1206-2289, 1987.

Pohl et al, "Qualitative Changes in Luteinizing Hormone and Prolactin Responses to N-Methyl-Aspartic Acid During Lactation in the Rat", *Endocrinology* 0013-7227/89/1244-1905, 1989.

Urbanski et al, "Activation of Luteinizing Hormone-Releasing Hormone Release Advances the Onset of Female Puberty", *Neuroendocrinology* 46: 273–276, 1987.

Farah, Jr. et al, "N-Methyl-D-Aspartate Treatment Increases Circulating Adrenocorticotropin and Luteinizing Hormone in the Rat", *Endocrinology* 0013-7227/91/1284-1875, 1991.

Cicero et al, "Characterization and Possible Opioid Modulation of N-Methyl-D-Aspartic Acid Induced Increases in Serum Luteinizing Hormone Levels in the Developing Male Rat", *Life Sciences*, Vol. 42, pp. 1725–1732, 1988.

Bourguignon et al, "Maturation of the Hypothalamic Control of Pulsatile Gonadotropin-Releasing Hormone Secretion at Onset of Puberty. I. Increased Activation of N-Methyl-d-Aspartate Receptors", *Endocrinology* 0013-7227/90/1272-087, 1990.

While the above publications suggest that there may be a link between the administration of NMA, or other amino acids, and levels of certain hormones in animals, none provides any teaching that the administration of NMA via injection provides enhanced growth or feed efficiency and/or a decrease in body fat comparable to that achieved with injection of GH.

Further, none of the above mentioned publications provides any teaching of the oral administration of NMA to provide enhanced growth, feed efficiency and/or decrease in body fat.

It is also noted that while the prior art teaches that NMA ingestion can result in an increase in GH, this has heretofore not correlated with an alteration in body composition. In broiler chickens, for example, daily intravenous injections of GH have been shown to increase growth rate, but not affect feed efficiency or carcass composition. See, Cravener et al, "Effect of Subcutaneous Infusion of Pituitary-Derived Chicken Growth Hormone on Growth Performance of Broiler Pullets", *Poultry Science* 68: 1133–1140, 1989.

SUMMARY AND OBJECTS OF THE INVENTION

It is accordingly a primary object of the invention to provide a method for increasing growth rate, feed efficiency and/or decreasing the body fat of an animal.

It is another object of the invention to provide a method, as above, which provides the requisite effect at a lower cost than the prior art use of growth hormone injections.

Briefly, the present invention relates to a method for increasing the growth rate, feed efficiency and/or for decreasing the amount of body fat of an animal, e.g., bovine, porcine or human, or other animal, e.g., avian species and aquatic species, which comprises administering to the animal N-methyl-d-aspartic acid, N-methyl-l-aspartic acid, N-methyl-d,l-aspartic acid, or a physiologically acceptable salt thereof. NMA can be administered by intravenous, intramuscular or subcutaneous injection, orally, subcutaneously or transdermally.

For purposes of the present application, the term animal includes humans as well as other animal species identified herein. While usually the term mammal is used to include humans, the term mammal is only one subset of the variety of species encompassed by the present invention.

DETAILED DESCRIPTION OF THE PREFERRED EMBODIMENTS

As hereinafter used, the terms "NMA" and "N-methyl-aspartic acid" refer to a mixture of the d and l isomers of the acid (i.e., a racemic mixture) which is the most readily available form of the acid. Generally, the optically active d and l isomers are isolated only at great expense and such isolation has not been found necessary to carry out the present invention. While the invention is not to be limited thereto, it is believed that the d isomer is likely the most physiologically active form, and if the pure d isomer is used, then the dosages disclosed hereinafter may be reduced accordingly.

The method of the invention may be carried out via injection, or by oral or transdermal administration or by subcutaneous implant of NMA. Oral administration of NMA is possible since, unlike complex compounds such as GH, NMA is a relatively simple compound which passes intact into the digestive tract. NMA can be administered to both mammalian, e.g., porcine, bovine and humans, and avian species, as well as to aquatic species such as fish, to effect the above noted changes in growth rate, feed efficiency and/or body fat content.

Generally, the amount of NMA required to significantly affect growth or body fat content is related to the route of administration. The amount is dependent on a number of factors and can be readily determined by one skilled in the art. For oral administration, daily dosages of from about 5 mg NMA/kg body weight (BW) to about 150 mg NMA/kg BW may be used, desirably from about 10 mg to about 100 mg NMA/kg BW, and preferably from about 10 to about 50 mg NMA/kg BW. Dietary levels of from about 10 to about 50 mg NMA/kg BW will effect significant changes in feed efficiency and body composition with the middle dosages (25 to 37.5 mg NMA/kg BW) having the greatest effect. The highest dosage, however, results in minimal or no benefit. For example, chickens fed about 50 mg NMA/kg BW had body fat and feed efficiency levels similar to untreated birds.

Surprisingly and unexpectedly, it has been found that while they improve feed efficiency and reduce carcass fat, dietary levels of from about 10 to about 50 mg NMA/kg do not substantially affect the blood levels of insulin-like growth factor (IGF-1) and other hormones. By contrast, when injecting NMA, single injection dosages of from about 0.5 to about 15 mg/kg BW will effect significant changes in IGF-1.

Preferably, the administration of NMA is maintained during the growth phase of the animal. For birds, such as broiler meat-type chickens, it is preferred that administration occur between the 5th and 7th week after hatching and continue for a period of at least 2 to 3 weeks. For other species, such as pigs, administration should begin at 125 days of age and continue for approximately 2 months. For bovines (e.g. cattle) NMA may be administered beginning at approximately six months of age and continued for approximately six months. Fish can be administered NMA orally beginning as hatchings and continuing up to the time of harvest. The specific period of administration can, of course, vary depending on the species and the target weight and fat content desired. One skilled in the art can readily select the appropriate administration period as well as dosage for a given situation.

In humans, NMA can be administered orally, by intravenous, intramuscular or subcutaneous injection, or transdermally as a single administration or it may be administered at a set interval for several years. The dose for humans would depend on a variety of factors, including the disease state being treated, the condition of the patient, the route of administration and the like. One skilled in the art could readily identify the desired dose for a given patient based on these factors. The dosage would preferably fall within other ranges of dosages for other animal species also set forth in this application.

NMA can be administered in the free acid form or, preferably, in salt form. When NMA is used as a salt, the cation can be any physiologically acceptable ion such as an alkali or alkaline earth metal, e.g., Li, Na, K, Mg, Ca, etc.

When NMA is injected, it is preferably in aqueous solution form having a concentration of from about 0.5 to about 4.0 molar, desirably from about 1.0 to about 3.0 molar and preferably from about 1.25 to about 2.25 molar. For use in oral administration, from about 125 to about 500 mg NMA/kg of feed product is used, with from about 250 to about 375 mg NMA/kg feed product preferred.

The NMA of the present invention can be administered along with a pharmaceutically acceptable carrier. Such carriers depend upon the precise route of administration and are well known to those skilled in the art. For convenience, reference may be made to *Remington's Pharmaceutical Sciences* for an identification of pharmaceutically acceptable carriers.

Administration can also be effected transdermally, whereby NMA is applied to the skin of the animal and thereafter crosses the skin barrier into the bloodstream. Preferably, the NMA is contained in a medium such as a gel, polymer, or absorbent woven or non-woven fabric which is affixed to the skin or hide of the individual. It is also possible, but less preferred, to apply an NMA solution directly to the skin or hide of the individual.

In general, suitable transdermal devices include a reservoir containing a solution of NMA and a means for controlled release of the NMA from the reservoir to the skin. The device, in the form of a patch, is adhered to the skin or hide of the animal via a suitable adhesive. Controlled release of NMA from the reservoir may be effected by the reservoir itself (i.e., matrix diffusion), using, for example, a suitable gel in which the NMA is dispersed. Alternatively, a rate controlling membrane can be used in conjunction with the reservoir, whereby the NMA is transported from the reservoir into the rate controlling membrane, and thereafter to the skin or hide of the animal.

Suitable reservoirs and rate controlling membranes are well known, and one skilled in the art can readily devise a functional transdermal device from known techniques. Exemplary of techniques for preparing transdermal devices are those described in U.S. Pat. Nos. 3,598,122; 3,598,123; 4,286,592; 4,314,557; 4,379,454; 4,568,343; 4,758,434 and 4,781,924 which are hereby incorporated by reference in their entirety.

The size of the transdermal device and the amount of NMA in the reservoir is dictated in part by the characteristics of the particular species to be treated. Generally the amount of NMA absorbed via the transdermal device is similar to the amount administered via injection. The transdermal device is effective for at least 12 hours, desirably at least 24 hours and preferably at least 72 hours. Most preferably the transdermal device is effective for at least 7 days.

NMA can also be administered via subcutaneous implant. Suitable devices which may be easily modified for subcutaneous implantation of NMA are set forth in U.S. Pat. Nos. 5,150,718 and 5,156,851 which are hereby incorporated by reference in their entirety. Typically, implants may be prepared by coating particles of NMA with a polymer having an aqueous solubility providing for controlled release of the NMA over a period of days, weeks or months. Alternatively, it is possible to prepare an implant by dispersing NMA in a resin such as polyvinyl chloride (PVC) and subsequently curing the resin. In this manner, the NMA is dispersed in the resulting polymer matrix in a substantially homogeneous manner. One such process is disclosed in U.S. Pat. No. 4,758,434. As with transdermal administration, subcutaneous implantation results in absorption of NMA in amounts similar to the amount administered via injection.

For domesticated animals, the preferred route of administration would depend on the species of animal selected. For instance, the present inventors believe that an injectable (e.g., intramuscular, intravenous or subcutaneous) route of administration would likely be most suitable for meat chicken and pigs; the oral form of administration would likely be most suitable for chicken, pigs and fish, the transdermal route of administration would likely be most suitable for cattle, sheep, pigs and laying hens; and the subcutaneous implant would likely be most suitable for cattle, sheep, pigs and laying hens. For humans, as mentioned above, administration can be any of the above forms.

While not wishing to be bound by any theory and the invention is not to be limited thereby, the inventors believe that d-NMA is a secretagogue for GRF (Growth Hormone Releasing Factor), that is, d-NMA stimulates the secretion of GRF. The GRF in turn is believed to stimulate secretion of GH in the animal by activating an N-methyl-d-aspartate (NMDA) receptor. This mechanism is supported by the results of Example 8 described hereinafter.

The following examples are intended to provide illustrations of the invention, and should not be construed as limiting in any way the scope thereof.

EXAMPLES 1 AND 2

Two experiments were conducted to evaluate the effect of a single dose of NMA (10 to 50 mg NMA/kg BW) on thyroxin and insulin-like growth factor in chickens. The chickens were 6 weeks old and weighed an average of 2.0 kg.

The results of Example 1 indicate that chickens given a single IV dose of NMA at levels of 2.5, 5.0 or 10.0 mg/kg body weight had elevated levels of IGF-1 at ½ and i hour post injection. In Example 2, chickens were given a single oral dose of NMA by gavage to determine if NMA would stimulate IGF-1 release when absorbed across the gastrointestinal tract. The chickens were dosed with 10, 25 or 50 mg/kg BW. Ten mg NMA/kg BW produced the most stimulating increase in IGF-1 levels (15–20%).

EXAMPLE 3

A third experiment was conducted to determine the effect of daily feeding of NMA (0, 125, 250, 375 and 500 ppm) on growth, feed efficiency, body fat content, thyroxin and insulin-like growth factor in meat-type broiler chickens. The dietary levels of NMA in this example were selected to mimic daily intake levels ranging from 10–50 mg/kg BW per day when mixed into the feed.

One hundred and twenty female broiler chickens were selected from a larger population at three weeks of age and moved into individual cages. Birds were allotted in a randomized complete block design. Commercial starter feed was fed from 0–3 weeks followed by a grower feed from 4–7 weeks. NMA was added to the feed during weeks 5, 6 and 7. Birds and feed were weighed weekly starting at 21 days of age. Blood samples were taken at 28, 35, 42 and 48 days of age to determine blood IGF-I, triiodothyronine and growth hormone levels. The birds were processed at 49 days of age (after an overnight fast) to determine % yield, % abdominal fat, and total body composition. The abdominal fat pad was also analyzed for lipid composition.

As seen in Tables 1 and 2, feeding NMA to commercial female broilers produced a curvelinear pattern in reducing percent abdominal fat pad (% ABF) and total carcass fat. Increasing levels of NMA from 0 to 250 ppm produced a significant linear decrease in percent ABF from 2.3% to 2.01% while feeding levels of NMA greater than 250 ppm resulted in a linear increase in percent abdominal fat pad from 2.01% to 2.37%. This curvelinear response was significant at $P<0.05$ with the maximal reduction in percent abdominal fat pad found in birds fed 250 ppm NMA. A similar pattern was detected in percent carcass shell fat. Increasing levels of NMA from 0 to 250 ppm produced a significant linear decrease in percent carcass shell fat from 11.00% to 9.65% while feeding levels of NMA greater than 250 ppm resulted in a linear increase in percent carcass shell fat from 9.65% to 10.38%. Feeding 250 ppm NMA resulted in a 12.55% decrease in percent ABF and a 12.26% decrease in carcass shell fat.

Weight gain and feed efficiency responses did not follow either a linear or quadratic pattern. Performance was similar for all levels of NMA, however, birds fed 375 ppm NMA had the highest average weight gain and gain/feed ratio. Day 48 blood levels of IGF-1 were not significantly affected by treatment.

Feeding graded levels of NMA produced a reduction in the percent abdominal fat and total body fat deposited by the chicken without any detrimental effect on weight gain and/or feed efficiency.

EXAMPLE 4

Example 3 was repeated except that larger birds were used which were raised in groups of 4 in litter floor pens. The results are summarized in Tables 3 and 4. The average weight gain in general was higher than in Example 3 but was unaffected by treatment. Similar to the results of Example 3, feed efficiency (gain/feed) was improved by adding NMA to the diet. The greatest improvement (+7.6%) was seen in birds fed 375 ppm NMA. Both % abdominal fat and % carcass shell fat were reduced by adding NMA. As in Example 3, the pattern was curvelinear with 375 ppm NMA giving the greatest reduction (3.32% vs 2.89% ABF and 11.85 vs 10.44% carcass shell fat for 0 vs 375 ppm NMA, respectively).

Both Examples 3 and 4 show that broilers fed 250–375 mg NMA/kg diet had significant reductions in body fat of 9–12%.

TABLE 1

(Example 3)

| DIET | WEIGHT GAIN (g) (DAYS 28–49) | GAIN/FEED (DAYS 28–49) | % ABDOMINAL FAT PAD |
|---|---|---|---|
| Basal | 978$^{ab}$ | .444$^b$ | 2.30$^{ab}$ |
| Basal + 125 ppm NMA | 989$^{ab}$ | .457$^{ab}$ | 2.13$^{ab}$ |
| Basal + 250 ppm NMA | 946$^b$ | .449$^b$ | 2.01$^b$ |
| Basal + 375 ppm NMA | 1035$^a$ | .468$^a$ | 2.16$^{ab}$ |
| Basal + 500 ppm NMA | 990$^{ab}$ | .450$^b$ | 2.37$^a$ |
| REGRESSION ANALYSIS USING ORTHOGONAL COMPARISONS | | | |
| Linear effect | NS | NS | $P < .05$ |
| Quadratic effect | NS | NS | $P < .05$ |
| Cubic effect | NS | NS | NS |

NOTE: values within columns with different superscripts differ significantly at $P < .05$ using lease significant difference (LSD) comparisons. NS means not significant.

TABLE 2

(EXAMPLE 3)

| DIET | % CARCASS SHELL FAT | % CARCASS WATER | IGF-1 DAY 48 ng/ml | Thyroxin (T4) |
|---|---|---|---|---|
| Basal | 11.00$^a$ | 65.17$^c$ | 37.1 | 24.4 |
| Basal + 125 ppm NMA | 10.63$^{ab}$ | 65.64$^{abc}$ | 34.6 | 23.2 |
| Basal + 250 ppm NMA | 9.65$^c$ | 66.12$^{ab}$ | 34.4 | 23.1 |
| Basal + 375 ppm NMA | 9.98$^{bc}$ | 65.54$^{bc}$ | 42.7 | 23.7 |
| Basal + 500 ppm NMA | 10.38$^{abc}$ | 66.17$^a$ | 37.0 | 24.9 |
| REGRESSION ANALYSIS USING ORTHOGONAL COMPARISONS | | | | |
| Linear effect | $P < .05$ | $P < .05$ | NS | NS |
| Quadratic effect | $P < .05$ | NS | NS | NS |
| Cubic effect | NS | NS | NS | NS |

NOTE: values within columns with different superscripts differ significantly at $P < .05$ using LSD comparisons.

TABLE 3

(EXAMPLE 4)

| DIET | WEIGHT GAIN (g) (days 28–49) | GAIN/FEED (DAYS 28–49) | % ABDOMINAL FAT PAD |
|---|---|---|---|
| Basal | 1341$^a$ | .410$^a$ (100%) | 3.32$^a$ |
| Basal + 125 ppm NMA | 1300$^{ab}$ | .422$^a$ (102.9%) | 3.12$^{ab}$ |
| Basal + 250 ppm NMA | 1302$^{ab}$ | .429$^{ab}$ (104.6%) | 3.04$^b$ |
| Basal + 375 ppm NMA | 1284$^{ab}$ | .441$^b$ (107.6%) | 2.89$^b$ |
| Basal + 500 ppm NMA | 1263$^b$ | .419$^a$ (102.2%) | 3.32$^a$ |
| REGRESSION ANALYSIS USING ORTHOGONAL COMPARISONS | | | |
| Linear Effect | $P < .05$ | NS | NS |
| Quadratic Effect | NS | $P < .05$ | $P < .05$ |
| Cubic Effect | NS | NS | NS |

TABLE 4

(EXAMPLE 4)

| DIET | % CARCASS SHELL FAT | % CARCASS WATER | % TOTAL SHELL FAT (W/ABF) |
|---|---|---|---|
| Basal | 11.85$^a$ | 61.71$^a$ | 16.17$^a$ |
| Basal + 125 ppm NMA | 11.20$^b$ | 62.78$^{bc}$ | 15.28$^{bc}$ (−5.51%) |
| Basal + 250 ppm NMA | 10.68$^a$ | 62.75$^{bc}$ | 14.66$^{cd}$ (−9.35%) |
| Basal + 375 ppm NMA | 10.44$^c$ | 63.35$^c$ | 14.25$^d$ (−11.88%) |
| Basal + 500 ppm NMA | 11.18$^b$ | 62.39$^b$ | 15.54$^b$ (−3.88%) |
| REGRESSION ANALYSIS USING ORTHOGONAL COMPARISONS | | | |
| Linear Effect | $P < .05$ | $P < .05$ | $P < .05$ |
| Quadratic Effect | $P < .05$ | $P < .05$ | $P < .05$ |
| Cubic Effect | NS | NS | NS |

EXAMPLE 5

Controlled release by parenteral administration of NMA may be provided by the use of subcutaneous implants incorporating a sufficient quantity of NMA. Granules of NMA or a physiologically acceptable salt thereof can be coated with polyvinyl alcohol (PVA) having a nominal molecular weight (Mn) of 50,000 to provide coated pellets having a particle size of about 3 mm. The PVA coating can be applied to NMA granules in the form of an aqueous solution containing 10% by weight PVA. The PVA solution, in the form of a spray, is applied to the NMA pellets as the latter are tumbled in a rotating drum. Application of PVA is continued until a coating of 2.5% by weight of the total granule weight is achieved.

The coated granules may be surgically implanted subcutaneously via incision into the skin of the animal to be treated. The amount of the granules implanted would be sufficient to maintain a minimum blood level of NMA of 1 mg NMA/100 ml of blood for a period of 21 days.

This type of administration is suitable for larger animals such as pigs and cattle, as well as humans.

EXAMPLE 6

Controlled release by transdermal administration of NMA may be provided by application of a patch to the skin of the animal to be treated. The patch includes a 12 cm diameter reservoir made from nonwoven cotton attached to an aluminum foil backing. The reservoir contains 5000 mg NMA. The aluminum foil backing has a diameter of 16 cm with a 2 cm annulus not covered by the reservoir. Over the annulus is applied a layer of pressure sensitive adhesive. The patch is applied reservoir-side down onto the bare skin of the animal and adhered via the pressure sensitive adhesive.

The patch would provide a minimum blood level of NMA of 1 mg NMA/100 ml of blood for a 24-hour period.

EXAMPLE 7

Three hundred and fifty commercial broiler females (Peterson X Arbor Acre) were raised on a commercial broiler starter feed until they were four weeks of age. At 28 days of age all birds were weighed and wing-banded. One hundred and sixty closest to the average weight for the group were selected and allotted to treatments in a Randomized Complete Block [RCB] design (5T×8R/T×4 C/R). NMA was added to the feed during weeks 5, 6 and 7. Birds and feed were weighed weekly starting at 28 days of age. The birds were processed at 49 days of age (after an overnight fast) to determine % yield, % abdominal fat, and total body composition.

A premix of NMA was prepared for mixing into the final feed. The basal diet (no NMA) was used as a control, with NMA added in amounts of 100 ppm, 200 ppm, 300 ppm and 400 ppm. The results are summarized in TABLES 5A and 5B.

TABLE 5A (Example 7)

| DIET | Weight Gain (g) 28–49 Days | Gain/Feed (days 28–49) |
|---|---|---|
| Basal NMA | 1280 | .396 |
| Basal + 100 ppm NMA | 1315 | .397 |
| Basal + 200 ppm NMA | 1295 | .399 |
| Basal + 300 ppm NMA | 1329 | .408 |
| Basal + 400 ppm NMA | 1319 | .411 |
| REGRESSION ANALYSIS USING ORTHOGONAL COMPARISONS | | |
| Linear Effect | NS | P < .05 |
| Quadratic Effect | NS | NS |
| Cubic Effect | NS | NS |

TABLE 5B (Example 7)

| DIET | % Abdominal Fat Pad | % Shell | % Water | % Shell Fat (Ether Extract) |
|---|---|---|---|---|
| Basal NMA | 2.83$^a$ | 65.62$^a$ | 64.91$^{ab}$ | 10.03$^a$ |
| Basal + 100 ppm NMA | 2.90$^a$ | 65.56$^a$ | 65.30$^{ab}$ | 9.06$^{ab}$ |
| Basal + 200 ppm NMA | 2.84$^a$ | 65.41$^a$ | 64.59$^b$ | 9.57$^{ab}$ |
| Basal + 300 ppm NMA | 2.92$^a$ | 65.88$^a$ | 65.40$^{ab}$ | 9.25$^{ab}$ |
| Basal + 400 ppm NMA | 2.82$^a$ | 65.73$^a$ | 65.60$^a$ | 8.67$^b$ |
| REGRESSION ANALYSIS USING ORTHOGONAL COMPARISONS | | | | |
| Linear Effect | NS | NS | NS | P < .05 |
| Quadratic Effect | NS | NS | NS | NS |
| Cubic Effect | NS | NS | NS | NS |

Note: Values within columns with different superscripts differ significantly at P < .05 using LSD comparisons.

As seen from Table 5A, NMA produced no significant effect on body weight gain. Feeding graded levels of NMA produced a significant linear improvement in feed efficiency with a maximum improvement of 3.8% in birds fed 400 ppm.

NMA had no significant effect on % abdominal fat pad or % shell (TABLE 5B). However, NMA produced a significant linear decrease in % shell fat with a maximum decrease of 13.6% seen in birds fed 400 ppm.

EXAMPLE 8

The objective of this study was to determine mechanisms responsible for the increases in serum concentrations of GH that follow i.v. treatment with NMA (2.5 mg/kg BW) in barrows. Yorkshire barrows (96 kg BW) fitted with jugular vein catheters were employed, and for each experiment blood samples were collected every 15 minutes for 2 (Experiments 1 and 2) or 3 (Experiment 3) hours immediately before and immediately after treatments. In Experiment 1, barrows received NMA (n=4) or i.v. injections of 1.25 mg of the pure d (n=4) or 1 (n=4) isomers of NMA/kg BW. Concentrations of GH in serum were similar between groups before injection averaging 1.39±0.12 ng/ml (mean±SE). GH levels increased by 177% (P<0.025) after NMA treatment and by 245% (P<0.01) after injection of the pure d isomer of NMA. The pure 1 isomer of NMA had no effect on GH concentrations. In Experiment 2, barrows received NMA immediately after i.m. injection of saline (n=7) or ketamine (n=8; 19.9 mg/kg BW), an n-methyl-d-aspartate (NMDA) receptor antagonist. Serum GH concentrations were similar between groups before injections and averaged 1.27±0.14 ng/ml. NMA increased (P<0.01) GH levels by 289% in saline-pretreated barrows but had no effect in barrows pretreated with ketamine. In Experiment 3, barrows received NMA 3 hours after i.v. pretreatment with antisera to GH-releasing factor (GRF: 154 ml; n=4) or no pretreatment (n=4). Overall serum GH concentrations were 1.28±0.22 ng/ml before NMA and increased (P<0.05) after NMA by 166% in barrows receiving no pretreatment. NMA had no effect on GH levels in individuals receiving antisera to GRF. These results support the concept that N-methyl-d-aspartate stimulates GRF, and hence GH secretion, by activating a NMDA receptor.

What is claimed is:

1. A method for increasing the growth rate, feed efficiency and/or for decreasing the amount of body fat of a chicken in need of some compared to a control, comprising injecting said animal on a periodic basis with an effective amount of a compound selected from the group consisting of N-methyl-d-aspartic acid, N-methyl-l-aspartic acid, and mixtures thereof.

2. A method as claimed in claim 1, further including the step of measuring the weight gain of the chicken and adjusting the dosage and frequency of injections based on the measured weight gain.

3. A method as claimed in claim 1, wherein the compound is a racemic mixture of N-methyl-aspartic acid, and the dosage is from about 0.5 to about 15 mg/kg of body weight administered once a day.

4. A method for increasing the growth rate, feed efficiency and/or for decreasing the amount of body fat of a chicken compared to a control, comprising orally administering to said animal on a periodic basis an effective amount of a compound selected from the group consisting of N-methyl-d-aspartic acid, N-methyl-l-aspartic acid, and mixtures thereof.

5. A method as claimed in claim 4, further including the step of measuring the weight gain of the chicken and adjusting the dosage and frequency of oral administration based on the measured weight gain.

6. A method as claimed in claim 4, wherein the compound is a racemic mixture of N-methyl-aspartic acid, and the daily dosage is from about 5 mg/kg of body weight to about 150 mg/kg of body weight.

7. A method for increasing the growth rate, feed efficiency and/or for decreasing the amount of body fat of a chicken compared to a control, comprising transdermally administering to said animal on a periodic basis an effective amount of a compound selected from the group consisting of N-methyl-d-aspartic acid, N-methyl-l-aspartic acid, and mixtures thereof.

8. A method as claimed in claim 7, further including the step of measuring the weight gain of the chicken and adjusting the dosage and frequency of transdermal administration based on the measured weight gain.

9. A method for stimulating the production of growth hormone in a chicken comprising administering to the chicken N-methyl-d-aspartic acid, in an amount sufficient to stimulate the secretion of growth hormone releasing factor.

10. A method as claimed in claim 9, wherein the compound is administered via intravenous, intramuscular or subcutaneous injection.

11. A method as claimed in claim 9, wherein the compound is administered orally.

12. A method as claimed in claim 9, wherein the compound is administered via subcutaneous implant.

13. A method as claimed in claim 9, wherein the compound is administered transdermally.

* * * * *